US009481915B2

(12) United States Patent
Liu et al.

(10) Patent No.: US 9,481,915 B2
(45) Date of Patent: Nov. 1, 2016

(54) METHOD OF SCREENING DRUGS THAT PROMOTE LOXL1 EXPRESSION

(71) Applicant: SHANGHAI TENTH PEOPLE'S HOSPITAL, Shanghai (CN)

(72) Inventors: Xiaoqing Liu, Shanghai (CN); Ming Ying, Shanghai (CN); Lihua Jian, Shanghai (CN)

(73) Assignee: SUZHOU BIOWISETECH CO., LTD., Suzhou (CN)

( * ) Notice: Subject to any disclaimer, the term of this patent is extended or adjusted under 35 U.S.C. 154(b) by 485 days.

(21) Appl. No.: 13/884,272

(22) PCT Filed: Dec. 28, 2012

(86) PCT No.: PCT/CN2012/087854
§ 371 (c)(1),
(2) Date: May 9, 2013

(87) PCT Pub. No.: WO2014/063427
PCT Pub. Date: May 1, 2014

(65) Prior Publication Data
US 2014/0302181 A1    Oct. 9, 2014

(51) Int. Cl.
*C12N 5/00*    (2006.01)
*C12Q 1/68*    (2006.01)
*G01N 33/50*    (2006.01)
*A23L 1/30*    (2006.01)
*A23L 1/29*    (2006.01)
*A61K 45/06*    (2006.01)
*A61K 36/00*    (2006.01)

(52) U.S. Cl.
CPC .............. *C12Q 1/6897* (2013.01); *A23L 1/29* (2013.01); *A23L 1/3002* (2013.01); *A61K 45/06* (2013.01); *G01N 33/5023* (2013.01); *G01N 33/5044* (2013.01); *A61K 36/00* (2013.01); *G01N 2333/78* (2013.01); *G01N 2500/00* (2013.01)

(58) Field of Classification Search
USPC ........................................................ 435/325
See application file for complete search history.

(56) References Cited

U.S. PATENT DOCUMENTS 4,503,047 A * 3/1985 Banfi et al. ................... 424/755
7,255,856 B2 8/2007 Li et al.

OTHER PUBLICATIONS

Translation of CN 102146435, 2010.*
Translation of WO 2005/069975.*
Machine translation of Written Opinion for PCT/CN2012/087854, created Dec. 2015.*
Hyeong Gon Yu, et al, Increased Choroidal Neovascularization following Laser Induction in Mice Lacking Lysyl Oxidase-like 1, Journal, Jun. 2008, 2599-2605, vol. 49, No. 6, Investigative Ophthalmology & Visual Science, Richmond, USA.
Xiaoqing Liu, et al, Failure of Elastic Fiber Homeostasis Leads to Pelvic Floor Disorders, Journal, Feb. 2006, 519-528, vol. 168, No. 2, American Journal of Pathology, Bethesda, USA.
Xiaoqing Liu, et al, Elastic fiber homeostasis requires lysyl oxidase-like 1 protein, Journal, Feb. 2004, 178-182, vol. 36, No. 2, Nature Genetics, London, UK.
oLVX-IRES-ZsGreen1 Vector Information, Catalog, Jul. 13, 2010, 1-3, PR073579, Clontech Laboratories, Inc.

* cited by examiner

*Primary Examiner* — Michael Wilson
(74) *Attorney, Agent, or Firm* — Anova Law Group, PLLC

(57) ABSTRACT

The present invention discloses a drug screening method, drugs promoting extracellular matrix protein crosslinking and their applications, the said drug screening method, is used to screen out materials promoting the expression of LOXL1 gene, wherein, the said drug screening method contains the following steps: A, Construct the 2nd generation lentiviral vector used to control the ZsGreen expression by human LOXL 1 gene promoter. B, Infect human fibroblasts with the 2nd generation lentiviral vector, and construct the new human fibroblasts which integrate PLOXL1-ZsGreen components. C, Drug screening: Inoculate the said human fibroblasts integrating PLOXL1-ZsGreen components into culture medium. Add the analyte into the cell culture medium containing human fibroblast cells. After culturing, detect the green fluorescence intensity of these fibroblast cells, then decide if the analyte promotes LOXL1 gene expression by checking if the green fluorescence intensity is increased. The method provided by the present invention is easy to operate and widely applicable.

12 Claims, 11 Drawing Sheets

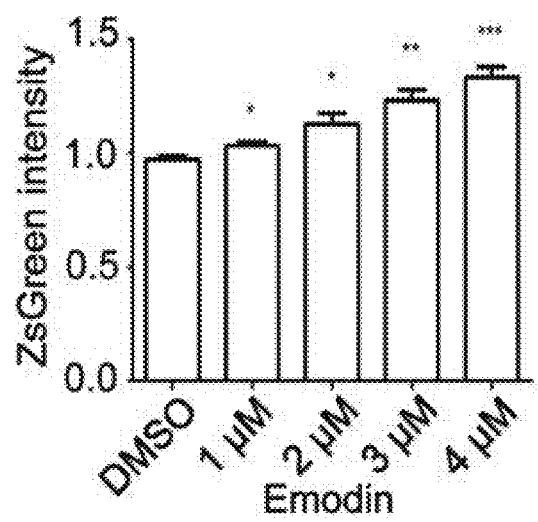
Figure 4c
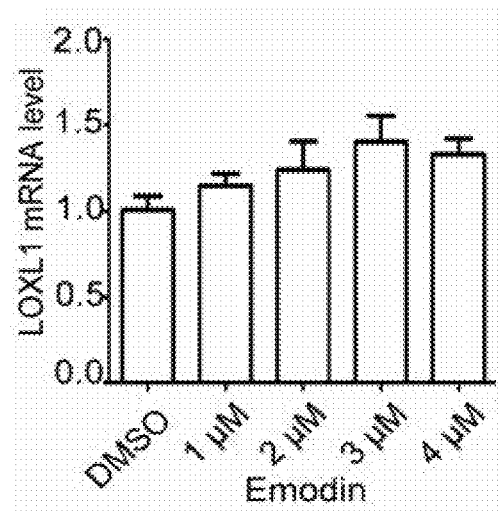
Figure 5a1

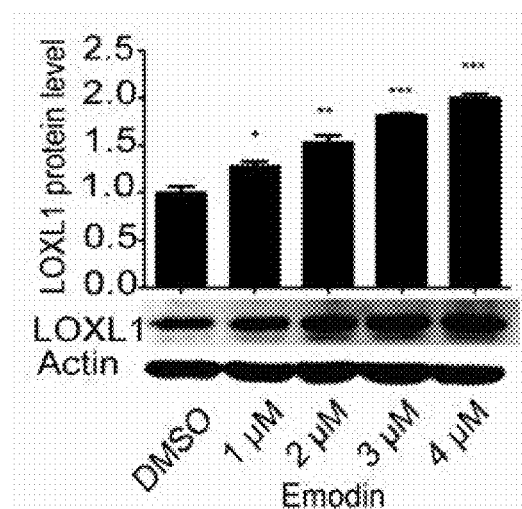
Figure 5a2
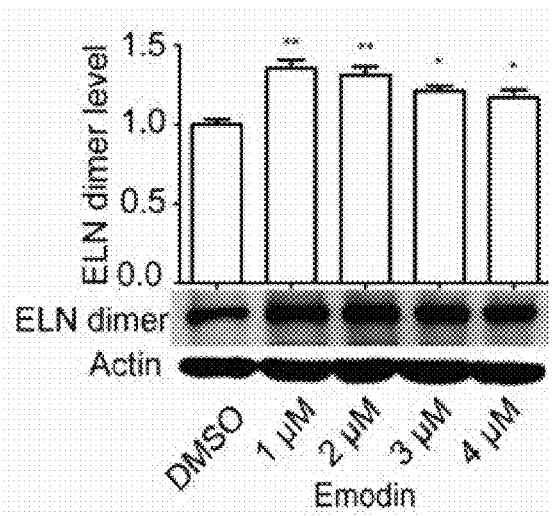
Figure 5a3

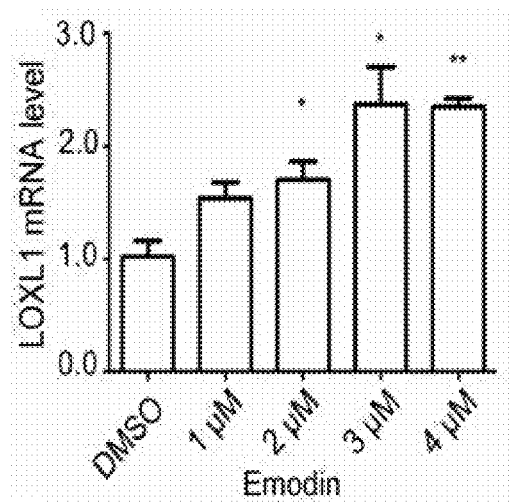
Figure 5b1
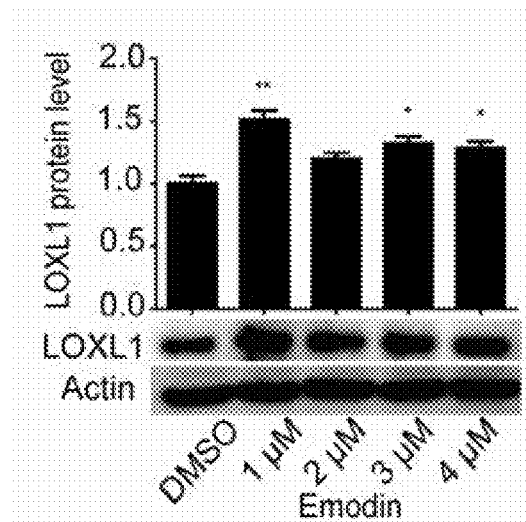
Figure 5b2

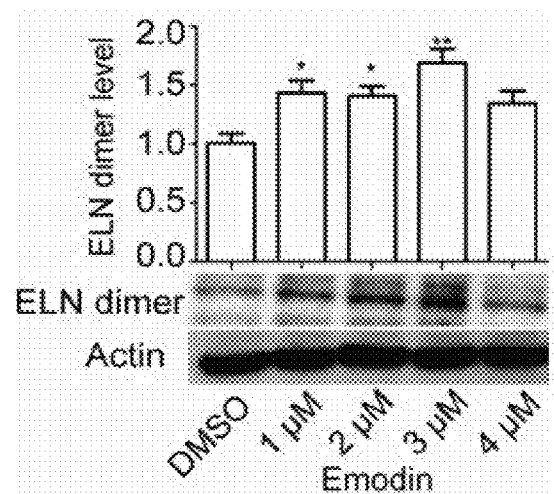
Figure 5b3
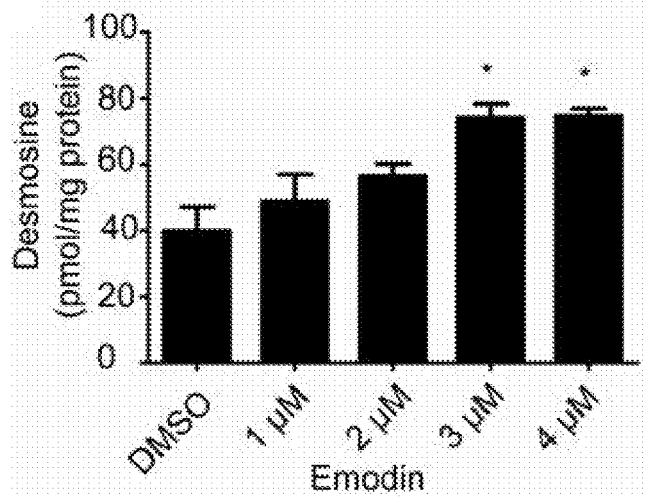
Figure 6a1

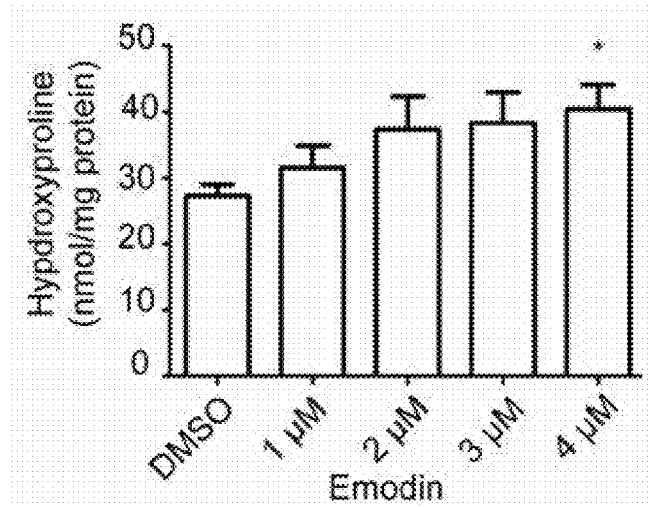
Figure 6a2
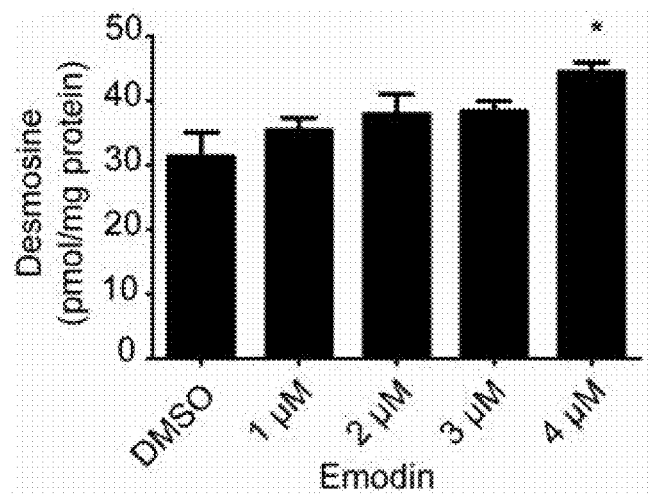
Figure 6b1

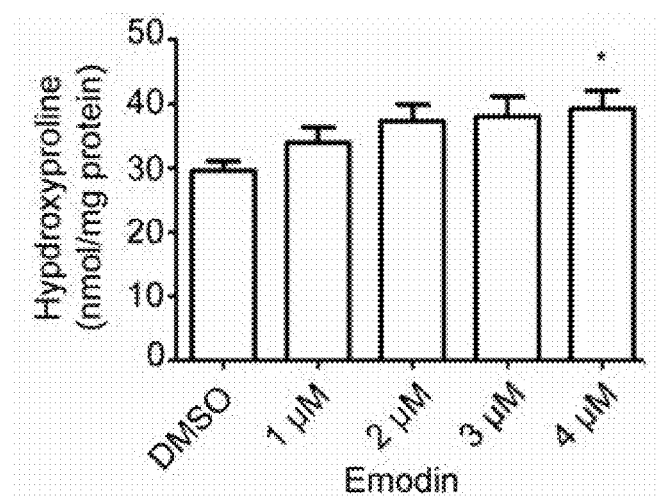
Figure 6b2
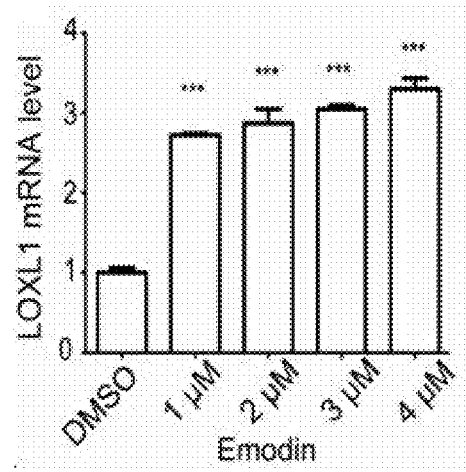
Figure 7a

SEQUENCE LISTING

```
<160> NUMBER OF SEQ ID NOS: 1

<210> SEQ ID NO 1
<211> LENGTH: 2060
<212> TYPE: DNA
<213> ORGANISM: Homo sapiens
<220> FEATURE:
<223> OTHER INFORMATION: Human LOXL1 gene promoter region sequence

<400> SEQUENCE: 1
agggatacac cccactcttc agactgggaa agtaagcccc tgaggtgtgc cacgagggaa      60
aaggtgcagc tccagtgcct ctcttcgcag gcccaagagc tgcggtgcac ctgggacctg     120
gaattagaga gtggtccctg ttcagcatct ccccgaggag gcccaccaac aaagagggtg     180
tgtctttttt ttttttttct tcctattgag ggtgtgggat aatggtggaa ggaacatgca     240
aagagggtgt gtcttaatta gcactggctt tagggaacaa ggaaaaggga gaacccggga     300
gtacgggaag gaggctgggg cagacaggag tcagaggccc attccagccc aaacgagaag     360
ccagtgagca aggtggagac cagggatgct gtgaccaaag cagagaggaa tgggcggggt     420
ggtgctgaca ccccagcccc gttctgcctg ccagagcccc acttaccagg cccgagtccc     480
cagaggtccc ctcctactcc ctgctcgatt cccttcctca gaggcaggtc tgtggcttgg     540
ctgggaactc cagggactga gggagcactg cagctgtggg accggcgcat agctaaaagc     600
cggcgggcca tagggccccg cggaggaggc cccagcaggc ggaccaggag gccgaagcct     660
cccgacgctc ccagcctgtt gcttattcat tcagagtggg aaagcgccag ccgagcggcc     720
agccagtgcg gggctggcca tgtaaggccc acaggcggtc ctgcccgccc ggtgccctgc     780
ggagagcctc gtgcagccct gggcaccgcc cctgccctgc cctgacccct tggccttgaa     840
atgctgtcat cggaggagcc gtcccgctcg ggacaaggcc agcatggaca aagctagagc     900
tggggcaagc aaggagcctt cctgtcctcg aggccgtggg aagagaagca cgcccagggg     960
gccactcctg agagcctctc tgtccaccag gcctctgcag aggggtcacc accggtcgcc    1020
accatggccc agtccaagca cggcctgacc aaggagatga ccatgaagta ccgcatggag    1080
ggctgcgtgg acggccacaa gttcgtgatc accggcgagg gcatcggcta ccccttcaag    1140
ggcaagcagg ccatcaacct gtgcgtggtg gagggcggcc ccttgccctt cgccgaggac    1200
atcttgtccg ccgccttcat gtacggcaac cgcgtgttca ccgagtaccc ccaggacatc    1260
gtcgactact tcaagaactc ctgccccgcc ggctacacct gggaccgctc cttcctgttc    1320
gaggacggcg ccgtgtgcat ctgcaacgcc gacatcaccg tgagcgtgga ggagaactgc    1380
atgtaccacg agtccaagtt ctacgcgtg aacttccccg ccgacggccc cgtgatgaag    1440
aagatgaccg acaactggga gccctcctgc gagaagatca tccccgtgcc caagcagggc    1500
```

```
atcttgaagg gcgacgtgag catgtacctg ctgctgaagg acggtggccg cttgcgctgc    1560
cagttcgaca ccgtgtacaa ggccaagtcc gtgccccgca agatgcccga ctggcacttc    1620
atccagcaca agctgacccg cgaggaccgc agcgacgcca agaaccagaa gtggcacctg    1680
accgagcacg ccatcgcctc cggctccgcc ttgccctaac tcgagtctag agggccccga    1740
cgcgtctgga acaatcaacc tctggattac aaaatttgtg aaagattgac tggtattctt    1800
aactatgttg ctccttttac gctatgtgga tacgctgctt taatgccttt gtatcatgct    1860
attgcttccc gtatggcttt cattttctcc tccttgtata aatcctggtt gctgtctctt    1920
tatgaggagt tgtggcccgt tgtcaggcaa cgtggcgtgg tgtgcactgt gtttgctgac    1980
gcaaccccca ctggttgggg cattgccacc acctgtcagc tcctttccgg gactttcgct    2040
ttccccctcc ctattgccac                                                2060
```

METHOD OF SCREENING DRUGS THAT PROMOTE LOXL1 EXPRESSION

TECHNICAL FIELD

The present invention relates to the field of medicine, and more particularly to a drug screening method as well as drugs promoting extracellular matrix crosslinking and the applications thereof.

SEQUENCE LISTINGS

The instant application contains a Sequence Listing which has been submitted in ASCII format via EFS-Web and is hereby incorporated by reference in its entirety. The ASCII copy is named sequence.txt and is 2,959 bytes in size.

BACKGROUND ART

Elastic fibers provide flexibility for a variety of organs, and collagen works as the supporting role for our body. Now it is known that a decrease in the crosslinking degree of elastic fibers causes a series of diseases in connective tissues, such as skin relaxation, emphysema, cardiovascular abnormalities, macular degeneration induced by vascular hyperplasia, sexual organs prolapse and urine incontinence. These lesions are senile chronic diseases, although not lethal but greatly affect people's living quality. Therefore, elastic fiber development and maintenance in the body is an important means to improve people's living quality.

Elastin polymerization is an important process for elastic fibers to maintain their crosslinking. Early in 2004 and 2006, Liu and his colleagues found that Lysyl oxidase-like 1(LOXL1) is the key factor specified to maintain and update the development of elastic fibers. Loss of the specific effects from LOXL1 to direct the crosslinking formation of elastic fibers is known to result in a series of dynamic lesions in connective tissues, including skin relaxation, emphysema, cardiovascular abnormalities, macular degeneration induced by vascular hyperplasia, sexual organs prolapse and urine incontinence. Further studies have found that, along with the aging of tissues and organs, the level of LOXL1 is greatly reduced, accompanied by the decline of crosslinking in elastin fibers and/or an increase in elastin monomers. These findings reveal that it is possible to delay the aging process of extracellular matrix in biological organisms by enhancing the expression levels or activity of LOXL 1 protein. (Nature Genetics 2004 (36): 178, Am J Path 2006 (168): 519 IOVS; 2008 (49): WO/2005/069975, 2599; U.S. Pat. No. 7,255,856, U.S. Pat. No. 7,255,857, European patent EP1706139).

However, in prior art, there is no drug screening method applicable to screen out a material which can effectively promote the expression level or activity of the LOXL1 protein.

BRIEF SUMMARY OF THE INVENTION

In view of the defects of the prior art, the aim of present invention is providing a drug screening method, drugs promoting extracellular matrix crosslinking as well as their applications, in order to solve the problem that there is no way to effectively screen out a material which is able to promote the expression level or activity of LOXL1 protein effectively.

The technical scheme of the invention is as follows:

A drug screening method used to screen out the materials promoting the expression of the LOXL1 gene, wherein, the said drug screening method comprises the following steps:

A. Construct the 2nd generation lentiviral vector used to control the ZsGreen expression by human LOXL 1 gene promoter: Cloning the human LOXL 1 gene promoter fragment into lentiviral vector, pLVX-ZsGreen, substituting its original CMV promoter, achieving the 2nd generation lentiviral vector, pLenti-$P_{LOXL1}$-ZsGreen, which contains the component of $P_{LOXL1}$-ZsGreen, used to control the ZsGreen expression through human LOXL1 gene promoter.

B. Infect human fibroblasts with the 2nd generation lentiviral vector, and construct the new human fibroblasts which integrate $P_{LOXL1}$-ZsGreen components.

C. Drug screening: Inoculate the said human fibroblasts integrating $P_{LOXL1}$-ZsGreen component into culture medium and incubate overnight. Dissolve the analyte into DMSO and add into the cell culture medium containing human fibroblast cells. After culturing, detect the green fluorescence intensity of these fibroblast cells, then decide if the analyte promotes LOXL1 gene expression by checking if the green fluorescence intensity is increased.

The said drug screening method, wherein, the details on the said Step B are as follows:

Package the 2nd generation lentiviral vector, concentrate into a titer of virus particles no less than $1\times10^7$/ml, dilute into 1:100. Then, it is used to infect human fibroblasts with a cell density of 20%, and after that, by flow cytometers (FCM), human fibroblast cell lines with a stable integration of $P_{LOXL1}$-ZsGreen component are screened out.

The said drug screening method, wherein, the said analyte is dissolved in DMSO with a concentration of 0.2-2 mg/ml, as in the said step C. And the final concentration of analyte in the said cell culture medium is 1-10 μg/ml.

Drugs promoting the crosslinking of extracellular matrix, wherein, the said drugs contains the materials for promoting LOXL1 gene expression, and the said drugs are screened out with the above said drug screening methods.

The said drugs promoting the crosslinking of extracellular matrix, wherein, the said drugs comprise the following one or a plurality of *agkistrodon, folium isatidis, cephalotaxus fortunei*, white mustard seed, white *atractylodes rhizome*, licorice root, snakegourd fruit, *exocarpium benincasae*, mulberry fruit, rice, *cynanchum glaucescens, lasiosphaera, flos rosae chinensis, catechu*, rose, *rehmannia glutinosa libosch, herba lycopi*, golden cypress, carolina cranesbill herb, *agastache rugosus, herba eupatorii, semen sinapis*, motherwort herb, motherwort, *oroxylum indicum, stephania tetrandra, schisandra chinensis*, phoenix quinoa, tendril-leaved fritillary bulb, *rhizoma smilacis glabrae, semen vaccariae, curcuma aromatica, rhodiola rosea* or emodin.

The application of the said drugs promoting the crosslinking of extracellular matrix, wherein, they are applied as additives of cosmetics, food additives, or for the preparation of drugs to treat or improve those diseases due to dynamic connective tissue lesions.

The beneficial effects: The present invention provides a screening method to screen out the drugs promoting the activity of human LOXL1 promoter and expression of LOXL1. This method has an advantage of simple operation as well as an extensive applicability. The present invention has screened thousands of Chinese herbal medicine extracts and small chemical molecules, found a series of herbal extracts and small molecules which can improve the LOXL1 level in senile human body cells. These substances can effectively promote the human LOXL1 promoter activity and LOXL1 expression, so as to promote the crosslinking of extracellular matrix proteins, which include, but not limited to elastin and collagens. Therefore, the said drugs which are used to promote extracellular matrix crosslinking can be applied as additives of cosmetics, food additives, or for the preparation of medicines to treat or improve those diseases due to dynamic connective tissue lesions.

DESCRIPTIONS OF THE DRAWINGS

FIG. 1 is a schematic view illustrating the coloning of human LOXL1 gene promoter and the construction of the stable fibroblast cell lines with active fluorescent tracers of human LOXL1 gene promoter in example 1 in the present invention.

FIG. 2 is the detection result view illustrating the fluorescent intensity of ZsGreen with and without herbal medicines treatment in example 2 in the present invention FIG. 3a is the detection result view illustrating the fluorescent intensity of ZsGreen after 32 herbal medicines treatment in example 3 in the present invention FIG. 3b is an experimental result view illustrating the western blot experimental results of cell extracts after drug treatments as in example 3 in the present invention.

FIG. 4c is a detection result view illustrating the fluorescent intensity of ZsGreen with different concentrations of emodin treatments in example 4 in the present invention.

Figure 1:
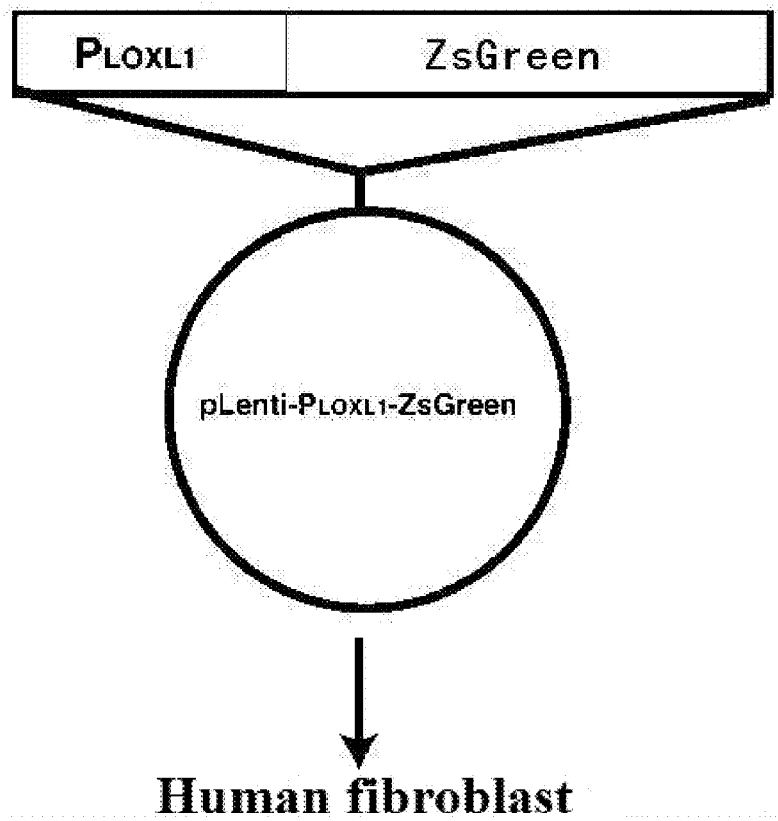

FIG. 5a1 is a view illustrating the mRNA level of human LOXL1 gene in human fibroblast cell line HF1 with and without emodin treatment in example 5 in the present invention.

Figure 2:
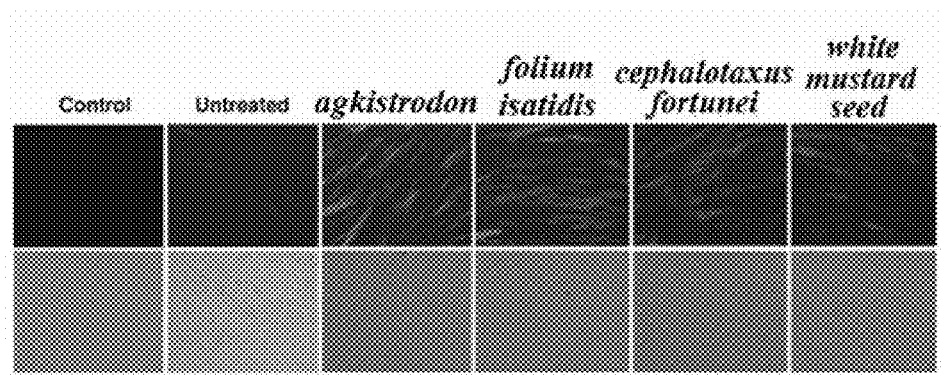

FIG. 5a2 is an experimental result view illustrating the western blot experimental results of human LOXL1 level in human fibroblast cell line HF1 with and without emodin treatments in example 5 in the present invention.

FIG. 5a3 is an experimental result view illustrating the western blot experimental results of human elastin dimer level in human fibroblast cell line HF1 with different concentrations of emodin treatments in example 5 in the present invention.

FIG. 5b1 is a view illustrating the mRNA level of human LOXL1 gene in human fibroblast cell line HF2 with and without emodin treatment in example 5 in the present invention.

FIG. 5b2 is a view illustrating the western blot experimental results of human LOXL1 level in human fibroblast cell line HF2 with and without emodin treatments in example 5 in the present invention.

FIG. 5b3 is an experimental result view illustrating the western blot experimental results of human Dimer level in human fibroblast cell line HF2 with different concentrations of emodin treatments in example 5 in the present invention.

FIG. 6a1 is an experimental result view illustrating the western blot experimental results of desmosine level in human fibroblast cell line HF1 with different concentrations of emodin treatments in example 6 in the present invention.

FIG. 6a2 is an experimental result view illustrating the western blot experimental results of Hydroxylproline level in human fibroblast cell line HF1 with different concentrations of emodin treatments in example 6 in the present invention.

FIG. 6b1 is an experimental result view illustrating the western blot experimental results of Desmosine level in human fibroblast cell line HF1 with different concentrations of emodin treatments in example 6 in present invention.

FIG. 6b2 is an experimental result view illustrating the western blot experimental results of Hydroxylproline level in human fibroblast cell line HF2 with different concentrations of emodin treatments in example 6 in the present invention.

FIG. 7a is a view of the mRNA level of LOXL1 gene in human skin with different concentrations of emodin treatments in example 7 in the present invention.

Figure 7B:
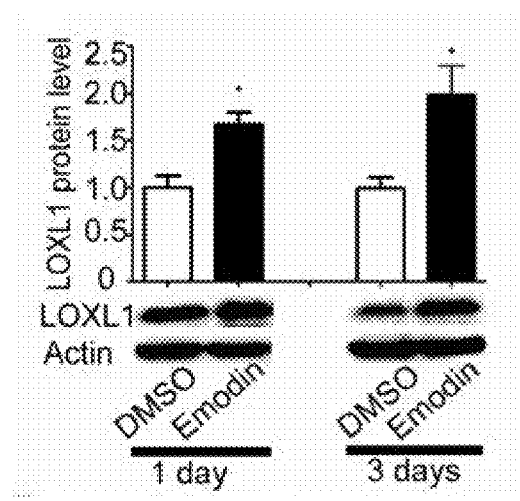

FIG. 7b is an experimental result view illustrating the western blot experimental results of LOXL1 level in human skin with a concentration of 4 µM emodin treatment in example 7 in the present invention.

Figure 7C:
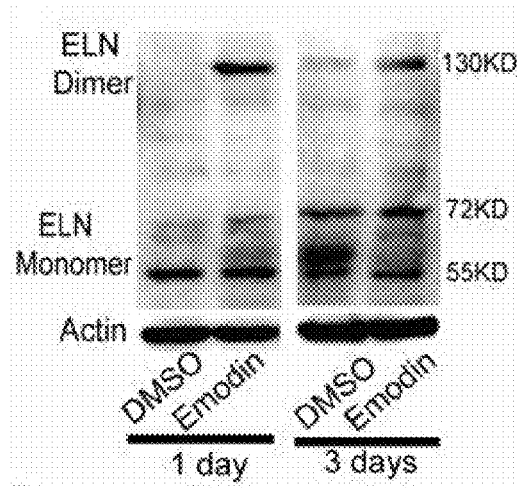

FIG. 7c is an experimental result view illustrating the western blot experimental results of elastin monomer level and dimer level in human skin with a concentration 4 µM emodin treatment in example 7 in the present invention.

DETAILED DESCRIPTION OF THE INVENTION

The present invention provides a drug screening method, drugs promoting the crosslinking of extracellular matrix and the applications thereof. In order to make the objective, technical solution and effect of present invention clearer and more explicit, detailed description of the invention is showing below. However, it should be understood that the embodiments described here are applied to explain the current invention only, instead of limiting the current invention.

Through the drug screening method provided by the present invention, drugs which can effectively promote the human LOXL1 promoter activity and LOXL1 expression can be screened out. With the drug screening method in the present invention, through the screening of thousands of Chinese herbal extracts and small chemical molecules, a series of Chinese herbal extracts and small molecules which can improve the LOXL1 level in senile human body cells have been found. Through the systemic study of a small molecule called emodin, it has been found that emodin and other 34 herbal medicines can effectively promote the human LOXL1 promoter activity and LOXL1 expression, so as to promote the crosslinking of extracellular matrix proteins, which include, but not limited to elastin and collagens. Wherein, emodin also significantly promotes the expression of LOXL1 in human fibroblasts and human skin tissue as well as the crosslinking formation of extracellular matrix.

The details of the said drug screening method include the following steps.

S1. Construct the 2nd generation lentivirus vector which contains fluorescent protein tracer, ZsGreen (a green fluorescent protein), whose expression is controlled by human LOXL1 gene promoter: through the Genscan software, predict about 3 kb genomic DNA fragments upstream the starting codon in human LOXL1 gene fragment, which is the promoter of human LOXL1 gene ($P_{LOXL1}$). Clone this fragment into lentivirus vector pLVX-ZsGreen (pLVX-IRES-ZsGreen1), substitute the original CMV promoter in pLVX-ZsGreen, then, the 2nd generation lentiviral vector (pLenti-P$_{LOXL1}$-ZsGreen) will be achieved, which contains fluorescent protein tracer ZsGreen whose expression is controlled by human LOXL1 gene promoter.

S2. Infect human fibroblasts with the 2nd generation lentiviral vector, and construct the new human fibroblast line which integrates P$_{LOXL1}$-ZsGreen components: Package the 2nd generation lentiviral vector, and concentrate into virus particles with a titer of no less than 1×10$^7$/ml, dilute into 1:100. Then, it is used to infect human fibroblasts with a cell density of 20%, and after that, by flow cytometers (FCM), human fibroblasts cell lines with a stable integration of P$_{LOXL1}$-ZsGreen component are screened out. The said human fibroblast line integrates an expression cassette (P$_{LOXL1}$-ZsGreen) tracing the activity of human LOXL1 promoter by ZsGreen fluorescent intensity.

S3. Drug screening: Inoculate the said human fibroblasts integrating P$_{LOXL1}$-ZsGreen component into culture medium, incubate overnight. Dissolve the analyte into DMSO as 0.2-2 mg/ml, and dilute into 1:200, then add it into the cell culture medium, and its final concentration will be 1-10 mg/ml. After incubating overnight (37° C., 5% $CO_2$), detect the green fluorescence intensity of these cells. The screening method of present invention decides if the analyte added stimulates the activity of human LOXL1 promoter effectively, and increases the expression of LOXL1, thus promotes the crosslinking of extracellular matrix protein, by checking if the green fluorescence intensity is increased.

By the said drug screening method, from two thousands of Chinese herbal medicines and a variety of small chemical molecules, it has been found that, there are 34 herbal medicines together with emodin significantly promoting the activity of LOXL1 promoter. Thus, the present invention also provides a drug which promotes the crosslinking of extracellular matrix protein, the said drug includes the following one or a plurality of *agkistrodon, folium isatidis, cephalotaxus fortunei*, white mustard seed, white *atractylodes rhizome*, licorice root, snakegourd fruit, *exocarpium benincasae*, mulberry fruit, rice, *cynanchum glaucescens, lasiosphaera*, fibs *rosae chinensis, catechu*, rose, *rehmannia glutinosa libosch, herba lycopi*, golden cypress, carolina cranesbill herb, *agastache rugosus, herba eupatorii, semen sinapis*, motherwort herb, motherwort, *oroxylum indicum, stephania tetrandra, schisandra chinensis*, phoenix quinoa, tendril-leaved fritillary bulb, *rhizoma smilacis glabrae, semen vaccariae, curcuma aromatica, rhodiola rosea* or emodin.

The application of the said drugs promoting the crosslinking of extracellular matrix protein is also provided in the present invention. The said drugs promoting the crosslinking of extracellular matrix protein can be applied as additives of cosmetics, food additives, or for the preparation of medicines to treat or improve those diseases due to dynamic connective tissue lesions. This kind of disease includes tissue aging disease caused by extracellular matrix protein crosslinking defects, such as skin relaxation, emphysema, cardiovascular abnormalities, macular degeneration induced by vascular hyperplasia, sexual organ prolapse and urine incontinence. Since the said drugs promoting extracellular matrix protein crosslinking can promote the expression of crosslinking enzyme LOXL1, improve the crosslinking rate of elastic fibers, thus, delay the aging process of extracellular matrix protein in biological organisms, and treat or improve connective tissue diseases.

Further explanation and description for the present invention are achieved by the following examples.

Example 1

Cloning Human LOXL1 Gene Promoter and Constructing the Stable Fibroblast Cell Lines with Active Fluorescent Tracers Through the Genscan software, predict about 2.16 kb genomic DNA fragments upstream the starting codon in human LOXL1 gene fragment (PLOXL1), whose sequence is shown as SEQ ID NO.1. Clone this fragment into lentivirus vector pLVX-ZsGreen, substitute its original CMV promoter, and the 2$^{nd}$ generation of lentiviral vector (pLenti-P$_{LOXL1}$-ZsGreen) is achieved, which contains fluorescent protein tracer ZsGreen whose expression is controlled by human LOXL1 gene promoter. Package with the 2nd generation lentiviral vector, and concentrate into virus particles with a titer of no less than 1×10$^7$/ml, dilute into 1:100. Then, it is used to infect human fibroblasts with a cell density of 20%, and after that, by flow cytometers (FCM), human fibroblasts cell lines with a stable integration of P$_{LOXL1}$-ZsGreen component are screened out, as shown in FIG. 1. The said human fibroblast integrates an expresiion cassette (P$_{LOXL1}$-ZsGreen) tracing the activity of human LOXL1 promoter by ZsGreen fluorescent intensity.

Example 2

Herbal Medicine Screening for Promoting the Activity of Human LOXL1 Promoter

Inoculate the said human fibroblasts integrating P$_{LOXL1}$-ZsGreen component into culture medium with a density of 20%, keep adherent overnight. Dissolve the extracts from herbal medicine into DMSO as 0.2-2 mg/ml, then dilute into 1:200 and add into the cell culture medium, makes the final concentration of 1-10 µg/ml. After culturing overnight (37° C., 5% $CO_2$), detect the green fluorescence intensity of these cells. The present invention decides if the Chinese herbal extracts added stimulate the activity of human LOXL1 promoter effectively by checking if the green fluorescence intensity is increased. It is found that 34 Chinese herbal medicines have an obvious promotion to LOXL1 promoter activity. As shown in FIG. 2, wherein, "control" is the normal human fibroblast, "untreated" means cells without drugs treatment integrating with the expression cassette of P$_{LOXL1}$-ZsGreen, which are the stably expressing strain of human fibroblasts. Others are stably expressed strain of human fibroblasts integrating the expression cassette of P$_{LOXL1}$-ZsGreen, with *agkistrodon, folium isatidis, cephalotaxus fortunei*, or white mustard seed, added in their culture medium. In the case of adding *agkistrodon, folium isatidis, cephalotaxus fortunei*, or white mustard seed added, the fluorescent intensity has an obvious increase, which indicates that *Agkistrodon, folium isatidis, cephalotaxus fortunei*, and white mustard seed can promote the activity of LOXL1 promoter.

Example 3

Chinese Herbal Medicines Promote the Activity of Human LOXL1 Gene Promoter and the Expression of LOXL1

Figure 3A:
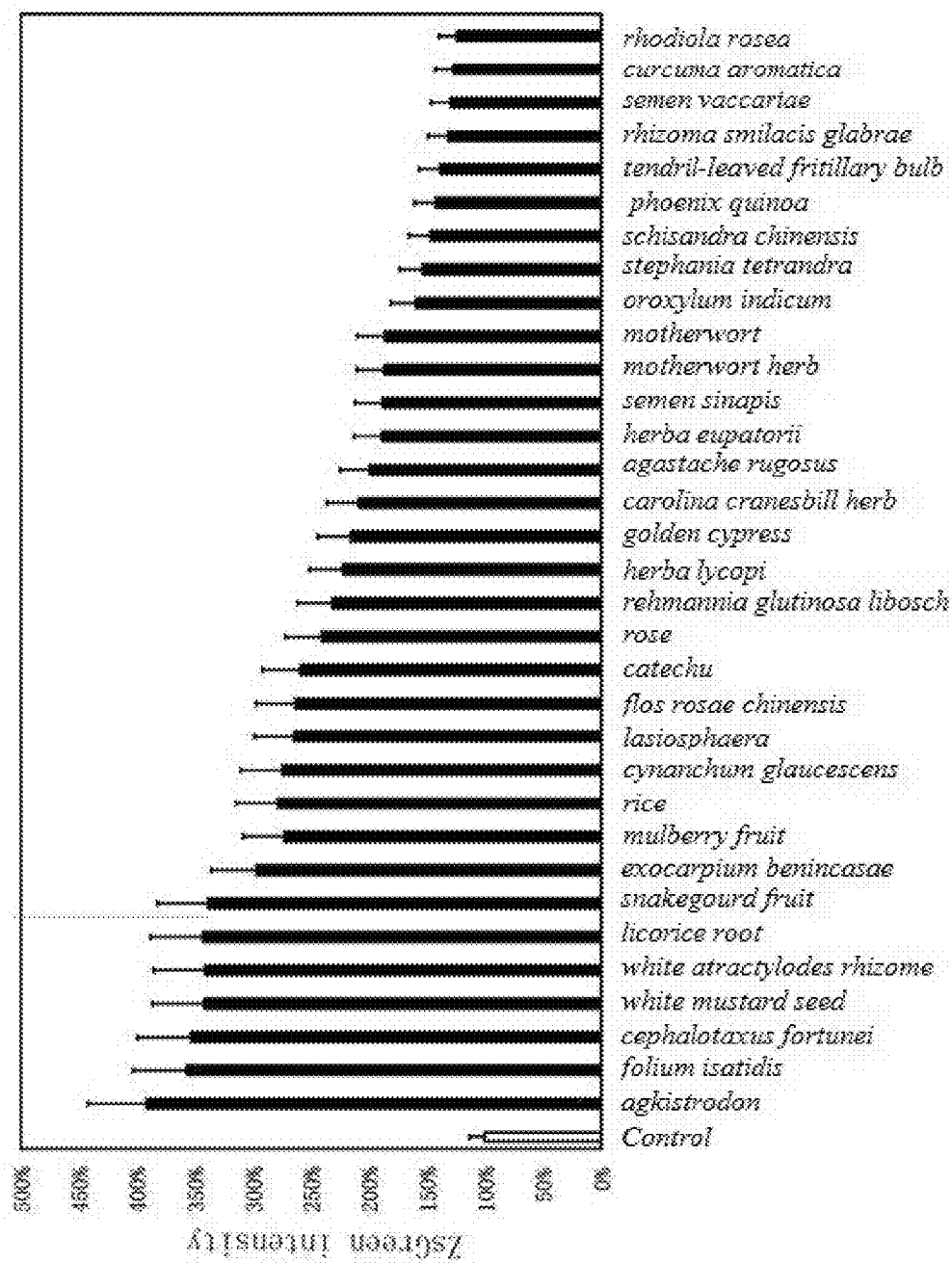
FIG. 3c is an experimental result view illustrating the western blot experimental results of cell extracts after drug treatments as in example 3 in the present invention.

Inoculate the said stably expressing human fibroblast strain integrating an expression cassette of P$_{LOXL1}$-ZsGreen with a 20% density into culture medium, incubate overnight, then dissolve the compounds into DMSO with a density of 0.2-2 mg/ml, dilute into 1:200 then add into the cell culture medium, makes the final concentration of 1-10 µg/ml. After culturing overnight (37° C., 5% $CO_2$), detect the green fluorescence intensity of these cells. As shown in FIG. 3a, "control" means that human fibroblast strain without drugs treatment integrating the expression cassette of $P_{LOXL1}$-ZsGreen is the stably expressing strain of human fibroblasts. The strain without drug treatments is normalized to 100%, all data are averaged with ±SEM of three independent experiments. FIG. 3a shows 32 Chinese herbal medicines promoting human LOXL1 promoter activity, which include *agkistrodon, folium isatidis, cephalotaxus fortunei*, white mustard seed, white *atractylodes rhizome*, licorice root, snakegourd fruit, *exocarpium benincasae*, mulberry fruit, rice, *cynanchum glaucescens, lasiosphaera, flos rosae chinensis, catechu*, rose, *rehmannia glutinosa libosch, herba lycopi*, golden cypress, carolina cranesbill herb, *agastache rugosus, herba eupatorii, semen sinapis*, motherwort herb, motherwort, *oroxylum indicum, stephania tetrandra, schisandra chinensis*, phoenix quinoa, tendril-leaved fritillary bulb, *rhizoma smilacis glabrae, semen vaccariae, curcuma aromatica* and *rhodiola rosea*.

Figure 3B:
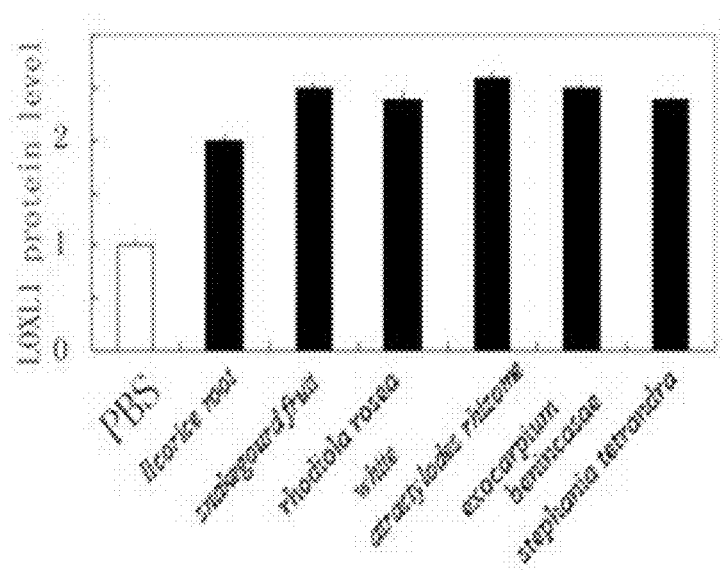
Figure 3C:
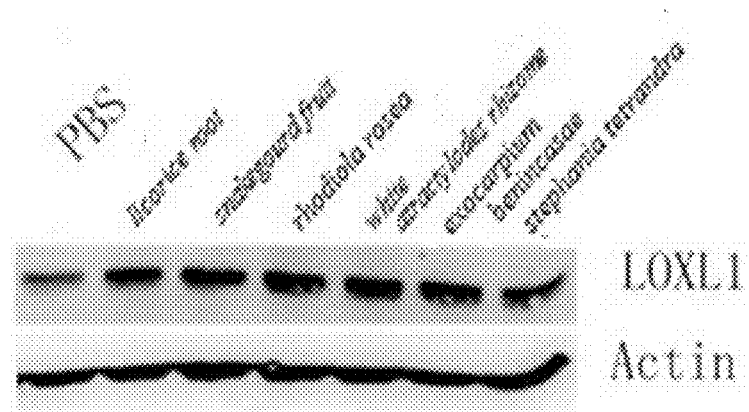

Randomly select several cell extracts after drug treatments and perform the western blot experiments, the results showed an obvious raising of LOXL1 protein in all cases, as shown in FIGS. 3b and 3c. "Control" means stably expressing strain of human fibroblasts without drugs treatment but integrating the expression cassette of $P_{LOXL1}$-ZsGreen. The figure shows that licorice root, snakegourd fruit, *rhodiola rosea*, white *atractylodes rhizome, exocarpium benincasae* and *stephania tetrandra* have an obvious promotion to human LOXL1 expression level. The strain without drug treatments is normalized to 1, all data are given as Mean±SEM, averaged by three independent experiments. Thus these Chinese herbal medicines improve the activity of LOXL1 promoter and increase the expression amount of LOXL1 in cells.

Example 4

Emodin Promotes LOXL1 Expression in Human Fibroblasts

Figure 4A:
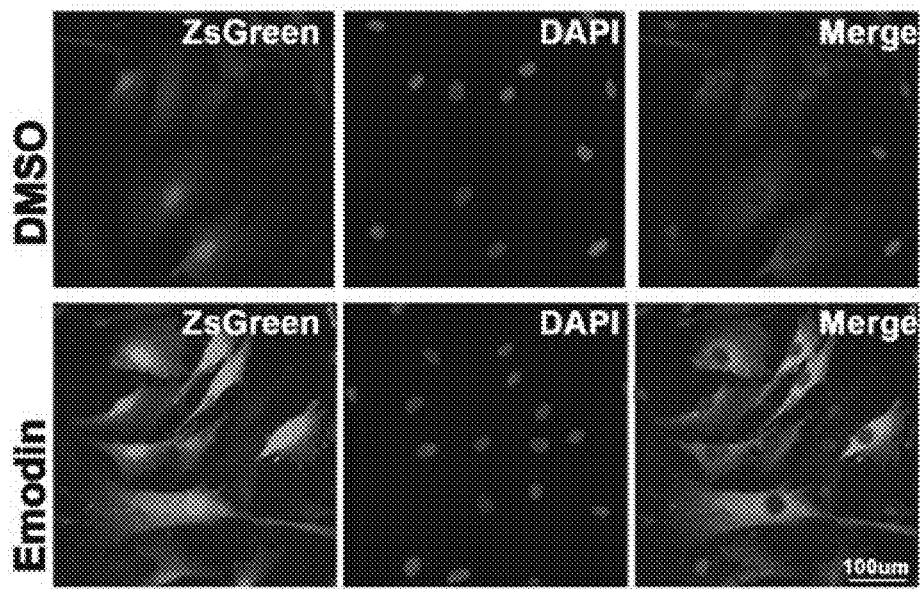
FIG. 4a is a detection result view illustrating the fluorescent intensity of ZsGreen with and without emodin treatments in example 4 in the present invention.
Figure 4B:
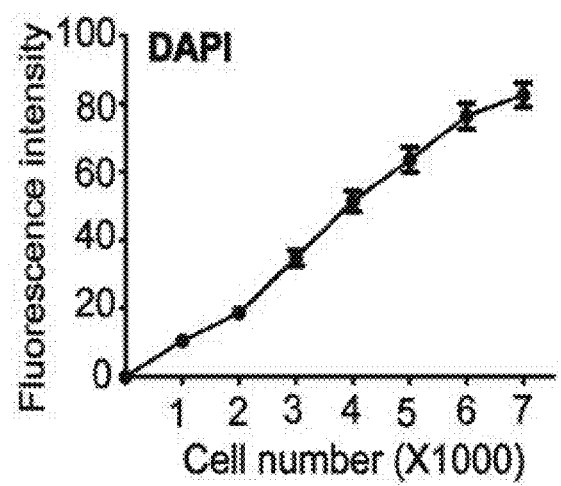
FIG. 4b is a detection result view illustrating the cell numbers with and without emodin treatments in example 4 in the present invention.

Inoculate the said stably expressing human fibroblast strain integrating a expression cassette of $P_{LOXL1}$-ZsGreen with a 20% density into media, keep adherent overnight (37° C., 5% $CO_2$), detect the green fluorescence intensity of these cells. It has been found that emodin has an obvious promotion to the activity of human LOXL1 promoter. As shown in FIG. 4a, the fluorescent intensity of ZsGreen tracer shows, emodin has an obvious promotion to the activity of human LOXL1 promoter (4 µM emodin). As shown in FIG. 4b, the fluorescent intensity of ZsGreen and the cell number indicated by Nuclear dye DAPI has a significant linear correlation. Data are calculated as Mean±SD, averaged by 5 independent test values. Thus, it is possible to trace the promoter activity through the fluorescent intensity of ZsGreen. As shown in FIG. 4c, the fluorescent intensity of ZsGreen increases with the concentration of emodin, with a significant linear relationship. Wherein, the control with DMSO added only, is normalized to 1, data are calculated as the Mean±SEM of three independent test values, *$P<0.05$; $P<0.001$; *$P<0.0001$.

Example 5

Emodin Promotes the Expression of LOXL1 in Human Fibroblasts

Two human fibroblast cell lines integrating $P_{LOXL1}$-ZsGreen components (HF1 and HF2) are inoculated at a density of 20%, incubated overnight (37° C., 5% $CO_2$). Emodin is added to the culture medium, and achieves a final concentration of 4 µM. After cultured overnight, Real-time and western blot are used to detect the mRNA level and protein level in LOXL1. Wherein, the one added DMSO solvent only works as the control, and is normalized to 1, data are calculated as Mean±SEM of three independent test values, *$P<0.05$; $P<0.001$; *$P<0.0001$. FIGS. 5a1~5a3 show the promotion of different emodin concentration to the expression of LOXL1 and the formation of elastin dimer intermediate in human fibroblast line HF1; FIGS. 5b1~5b3 show the promotion of different emodin concentration to the expression of LOXL1 and the formation of elastin dimer intermediate in human fibroblast line HF2. In these two cell lines, the expression of LOXL1 is not only linearly correlated to transcriptional level, but to LOXL1 protein level, and accomplishing elastin dimer intermediates formation. This example reveals that, emodin significantly promotes the expression of LOXL1 in HF1 and HF2 cell lines.

Example 6

Emodin Promotes the Crosslinking of Extra Cellular Matrix in Human Fibroblasts

Two human fibroblast cell lines integrating $P_{LOXL1}$-ZsGreen components (HF1 and HF2) are inoculated at a density of 20%, incubated overnight (37° C., 5% $CO_2$). Then, emodin is added into the culture medium. Detect the desmosine by ELISA method to determine the effects of different emodin concentrations to elastin crosslinking.

As shown in FIGS. 6a1~6a3, in human fibroblast line HF1, different emodin concentrations have a significant promotion to the expression of LOXL1 and the crosslinking of elastin. It is shown that the desmosine intermediates increase with the increasing concentrations of emodin added, accompanying with collagen crosslinking increases significantly, which is shown that hydroxylproline intermediate also increases with the increasing concentrations of emodin added. As shown in FIGS. 6b1~6b3, in human fibroblast line HF2, different emodin concentrations have a significant promotion to the expression of LOXL1 and the crosslinking of elastin. It is shown that the desmosine intermediates increase with the increasing concentrations of emodin added; At the same time accompanying with collagen crosslinking increases significantly, which is shown that hydroxylproline intermediate also increases with the increasing concentrations of emodin added. The data are calculated as Mean±SEM of three independent test values, *$P<0.05$.

This example determines the effects of different emodin concentrations to collagen crosslinking by detecting the contents of hydroxylproline through ELISA method. The experimental results show that, following the increase of emodin concentration, elastin crosslinking increases and the collagen crosslinking is also increasing in both HF1 and HF2 lines. Thus, emodin promotes the crosslinking of extracellular matrix protein in human fibroblasts widely.

Example 7

Emodin Promotes the LOXL1 Expression and Elastin Crosslinking in Human Skin

Emodin was added into the culture medium of human skin tissue. Detect the LOXL1 level in human skin tissue and elastin crosslinking level during 1~3 days after emodin treatment. Detect the mRNA level and protein level of LOXL1 using Real-time and western blot methods, as well as detecting the amount of monomer and dimer of elastin. Wherein, the control with DMSO solvent added only is normalized to 1, data are calculated as Mean±SEM of three independent test values. *p<0.01, ***P<0.0001.

As shown in FIG. 7a, LOXL1 mRNA level increases as the emodin concentration increases. As shown in FIG. 7b, adding 4 μM emodin significantly promotes the LOXL1 protein level. As shown in FIG. 7c, adding 4 μM emodin significantly promotes the elastin crosslinking formation, shown as the decrease of elastin monomers and increase of intermediate dimers.

The results in this example show that, with the increase of emodin concentrations, levels of LOXL1 mRNA and LOXL1 protein are also increasing gradually, and accompanying the increase of elastin crosslinking. Thus, emodin has a significant promotion to the expression of LOXL1 in human skin tissue and formation of elastin crosslinking.

It should be understood that, the application of the present invention is not limited to the above examples listed. It will be possible for a person skilled in the art to make modifications or replacements according to the above description, which shall all fall within the scope of the appended claims of the present invention.

The invention claimed is:

1. A method for screening drugs that promote LOXL1 gene expression in vitro, comprising:
   a) replacing the CMV-IE promoter of pLVX-IRES-ZsGreen1 with a LOXL1 promoter to obtain pLenti-$P_{LOXL1}$-ZsGreen;
   b) transfecting isolated fibroblasts with the pLenti-$P_{LOXL1}$-ZsGreen lentiviral vector;
   c) administering a drug dissolved in DMSO to the transfected fibroblasts;
   d) detecting green fluorescence intensity of the transfected fibroblasts of step c), wherein increased green fluorescence intensity indicates the drug promotes LOXL1 gene expression.

2. The method of claim 1, wherein, step b) further comprises:
   selecting fibroblasts with a stable integration of $P_{LOXL1}$-ZsGreen.

3. The drug screening method of claim 1, wherein, the drug is dissolved in DMSO with a concentration of 0.2-2 mg/ml and has a final concentration of 1-10 μg/ml in culture.

4. The method of claim 1, wherein the human LOXL1 promoter is a human LOXL1 promoter.

5. The method of claim 4, wherein the human LOXL1 promoter is 3 kb.

6. The method of claim 4, wherein the human LOXL1 promoter is 2.16 kb.

7. The method of claim 1, wherein step b) further comprises:
   packaging and concentrating the pLenti-$P_{LOXL1}$-ZsGreen lentiviral vector into viral particles; and
   diluting the viral particles before transfecting the fibroblasts.

8. The method of claim 6, wherein:
   the pLenti-$P_{LOXL1}$-ZsGreen lentiviral vector is packaged and concentrated into viral particles with a titer of no less than $1\times10^7$/ml.

9. The method of claim 7, wherein:
   the viral particles are diluted at a ratio of 1:100.

10. The method of claim 1, wherein:
    the fibroblasts have a cell density of 20% before transfection.

11. The method of claim 1, wherein:
    the fibroblasts are human fibroblasts.

12. The method of claim 2, wherein:
    the fibroblasts with a stable integration of $P_{LOXL1}$-ZsGreen component are selected using a flow cytometer (FCM).

* * * * *